United States Patent [19]
Van Mastrigt

[11] 3,974,686
[45] Aug. 17, 1976

[54] EXTENSOMETER FOR TENSILE TESTER

[75] Inventor: Max Van Mastrigt, Tarzana, Calif.

[73] Assignee: W. C. Dillon & Co., Inc., Van Nuys, Calif.

[22] Filed: Oct. 1, 1975

[21] Appl. No.: 618,414

[52] U.S. Cl. .............................. 73/95; 73/141 AB
[51] Int. Cl.² ......................................... G01N 3/08
[58] Field of Search ................. 73/95, 90, 141 AB; 33/147 D, 148 D

[56] References Cited
UNITED STATES PATENTS

| | | | |
|---|---|---|---|
| 1,961,368 | 6/1934 | Larson | 73/141 AB |
| 2,663,085 | 12/1953 | Ruge | 33/147 D |
| 3,295,365 | 1/1967 | Larrigan et al. | 73/95 |
| 3,782,188 | 1/1974 | Korber et al. | 73/141 AB |

Primary Examiner—Jerry W. Myracle
Attorney, Agent, or Firm—Ralph B. Pastoriza

[57] ABSTRACT

The extensometer has first and second gripping portions on spaced members designed to be applied to a specimen by using only one hand. Changes in the length of the specimen are indicated by an electrical signal derived from a flexure strain gage arrangement in one of the members against which a probe is urged by forces on the other member. The coupling of the probe to the other member is through a spring biasing arrangement such that the biasing force can be changed so that the strain gage flexure movements can be made constant for different percentage elongations to be measured.

7 Claims, 5 Drawing Figures

U.S. Patent  Aug. 17, 1976  3,974,686
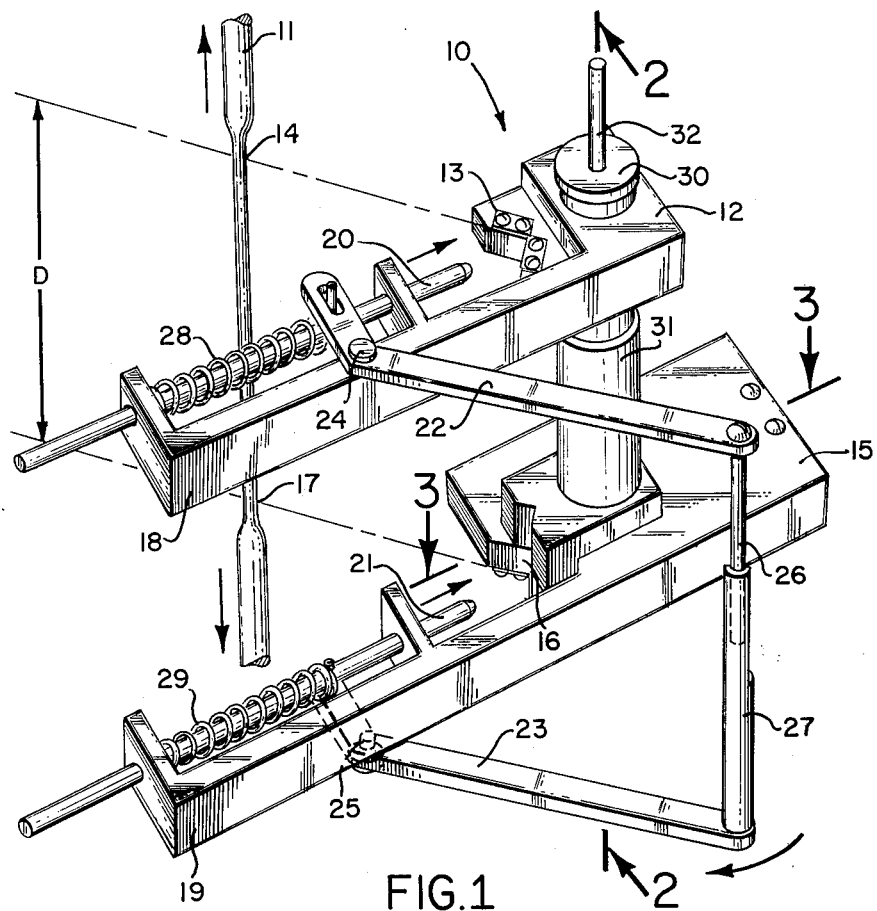
FIG.1
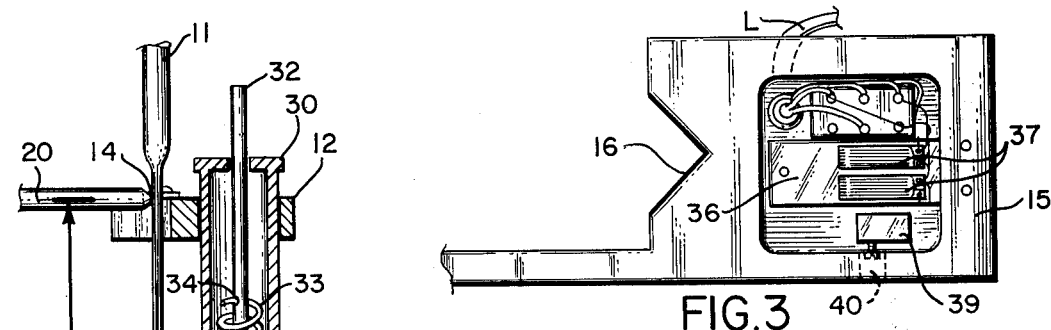
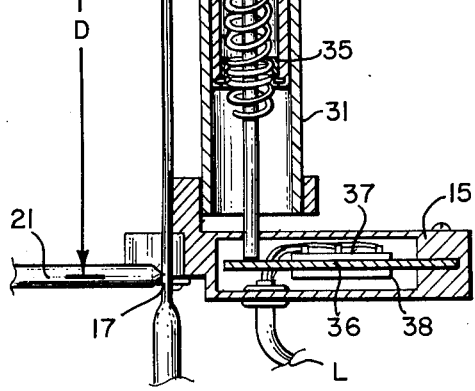
FIG.2
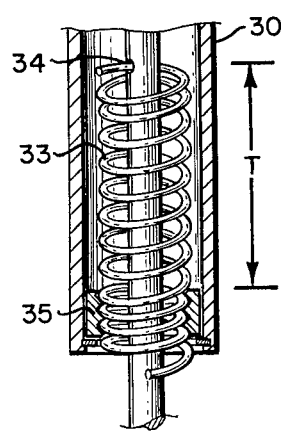
FIG.4
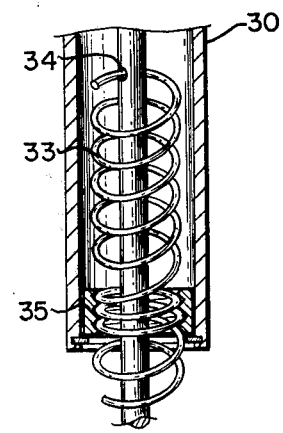
FIG.5

EXTENSOMETER FOR TENSILE TESTER

This invention relates generally to extensometers and more particularly, to an improved extensometer in which output indications are provided by force responsive strain gauges.

BACKGROUND OF THE INVENTION

Extensometers are instruments for measuring a change in elongation of a specimen under a stretching force. Thus in materials analysis, it is oftentimes desirable to know precisely the percent elongation of a member prior to rupture as well as the rupturing force.

Generally, it is desirable to provide a continuous direct read-out of the specimen elongation during a test. Towards this end, the more recently developed extensometers provide strain gage flexure means responsive to elongation of the specimen to provide an electrical signal from a strain gage bridge which may be properly calibrated to indicate the elongation. Typical extensometers of this type will include a pair of leg elements which can be secured at spaced points to the specimen under test, separation of the securement points of the legs as the specimen stretches providing flexure action which is measured by the strain gages in the device. U.S. Pat. No. 3,319,338 issued on May 16, 1967 illustrates a typical extensometer of this type.

In utilizing such extensometers, separate securing means are provided for securing the ends of each of the legs to spaced points on a specimen. The actual attachment of the extensometers as are presently available is somewhat awkward and time consuming in view of this particular type of design utilizing the separate securing elements. Moreover, care must be exercised to secure the ends of the legs at precisely spaced points on the specimen as otherwise a proper reference is not provided for measuring the elongation.

Finally, when more than one extensometer is being used for different gage lengths or different percents of maximum strain, no provisions have been made to allow for interchangeability between different extensometers and one recording instrument. It would be desirable to provide an extensometer which can accommodate different type specimens wherein different percentage elongations are to be indicated and yet wherein the flexure portions utilizing strain gages is always flexed a constant amount.

BRIEF DESCRIPTION OF THE PRESENT INVENTION

Bearing the foregoing considerations in mind, the present invention contemplates an improved extensometer of the type incorporating a flexure unit and strain gages but wherein various problems, such as outlined heretofore, associated with presently available extensometers are avoided.

More particularly, the extensometer of the present invention is so designed as to be readily applied to a specimen by using only one hand.

Moreover, the extensometer is designed in such a way that regardless of the gage length or the maximum strain required, the strain gage flexure element is always subjected to the same deflection, the same being accomplished by means of a spring adjustment.

Briefly, the invention comprises a first member defining a first gripping means for engaging a specimen at a first point; a second member defining a second gripping means for engaging a specimen at a second point; guide means coupling the first and second members together for movement towards and away from each other in response to changes in the distance between the first and second points on the specimen; a probe element and biasing means carried by the first member and connected to the probe element for biasing the probe element towards the second member. The assembly is completed by the provision of strain gage flexure means carried by the second member in a position to be engaged by the probe element and responsive to the force exerted by the probe element to provide an electrical signal constituting a function of this force.

With the foregoing arrangement, changes in the distance between the first and second points on the specimen will change the force and thus the output signal which may be converted to reflect the distance change.

Important features of this invention include a manual means operable by one hand for engaging the specimen with the extensometer and in addition adjustment means for the spring biasing the probe such that the deflection of the strain gage flexure portion can be made constant for different percent elongations to be measured by the instruments.

BRIEF DESCRIPTION OF THE DRAWINGS

A better understanding of this invention will be had by now referring to the accompanying drawings in which:

FIG. 1 is a perspective view of the extensometer preparatory to receiving a specimen, the elongation of which is to be measured;

FIG. 2 is a fragmentary cross section taken in the direction of the arrows 2—2 of FIG. 1 illustrating the specimen engaged by the extensometer;

FIG. 3 is a fragmentary plan view taken in the direction of the arrows 3—3 of FIG. 1;

FIG. 4 is an enlarged fragmentary cross section of a portion of the device illustrated in FIG. 2 showing a first spring adjustment; and, FIG. 5 is a view similar to FIG. 4 but showing the adjustment in a different position.

DETAILED DESCRIPTION OF THE PREFERRED EMBODIMENT

Referring first to FIG. 1 the extensometer is designated generally by the numeral 10 in a position preparatory to receiving a specimen 11 which may be in the form of an elongated rod or wire positioned in a suitable tension machine.

The extensometer itself includes a first member 12 defining a first gripping means 13 incorporating knife edges defining a V-shaped receiving portion for engaging a first point 14 on the specimen 11. A second member 15 similarly includes a second gripping means 16 including knife edges defining a V-shaped receiving opening for engaging a second point 17 on the specimen. The first and second points 14 and 17 on the specimen 11 are at a given distance apart designated D in FIG. 1 when the specimen 11 has no force applied to it. When the respective points are gripped by the first and second members 12 and 15, and a tension is applied to the specimen, any stretching or elongation will result in the first and second members 12 and 15 being separated or moving apart from each other.

With respect to the foregoing, it is important that the initial engagement of the specimen 11 take place at spaced points which are a known given distance D apart and thus the gripping means themselves must be positive in their securement at the precise points involved. Towards the end of providing a secure and non-redundant gripping of each of the points on the specimen, the members 12 and 15 respectively include support means 18 and 19 carrying opposing pins 20 and 21 juxtaposed the V-shaped receiving portions 13 and 16. These pins are arranged to engage the opposite sides of the specimen 11 when received in the V-shaped receiving knife edge portions as described. Thus for each point engaged on the specimen, there is essentially a three-point contact comprised of the two knife edges and the associated pin. The precise distance between the knife edges is known and made to correspond to the distance D so that the spaced first and second points 14 and 17 on the specimen 11 engaged by the extensometer will be at this corresponding distance.

An important feature of this invention is the fact that the extensometer may be applied to the specimen 11 with one hand rather than requiring the relatively long drawn-out process of applying separate clamps to the engaged points. This feature is accomplished by providing a manually operable means in the form of arms 22 and 23 pivoted to the supports 18 and 19 as at 24 and 25 for simultaneous swinging movement in a manner to urge the pins 20 and 21 towards and away from the opposed V-shaped receiving portions respectively. The simultaneous movement is effected by providing a rod 26 and cooperating semi-circular sleeve 27 directed towards each other at the ends of the arms 22 and 23 so that movement of the sleeve 27 in a direction to retract the pins will cause simultaneous movement of the rod 26 so that the arms 23 and 22 will move simultaneously.

Suitable springs 28 and 29 are provided normally biasing the pins 20 and 21 towards the V-shaped receiving knife edges 13 and 16 of the members as indicated by the arrows.

The extensometer described in FIG. 1 further includes a suitable guide means for coupling the first and second members 12 and 15 together for movement towards and away from each other in response to changes in the given distance D. This guide means includes first and second axially aligned cylinders 30 and 31 carried by the first and second members respectively. The first cylinder 30 has its lower end as viewed in FIG. 1 telescopically received in the second cylinder 31.

Cooperating with the guide means is a probe element 32 which is essentially carried by the upper member 12 and extends towards the lower member 15 within the cylinders 30 and 31.

The foregoing arrangement can better be understood by now referring to FIG. 2 wherein the telescoping relationship between the guide cylinders 30 and 31 is clearly shown. Also evident is the probe 32 axially positioned within the first cylinder 30 to extend through the second cylinder 31. A biasing means in the form of a spring 33 is connected to the probe as at 34 at one end and has its other end coupled to the lower end of the first cylinder 30 by coupling means 35. The arrangement is such that the spring 33 exerts a downward biasing force on the probe 32 as viewed in FIG. 2.

Also clearly shown in FIG. 2 is a strain gage flexure means 36 secured within the second member 15 and incorporating strain gages 37 and 38, the flexure itself constituting a cantilevered beam. This flexure is positioned to be engaged by the lower end of the probe element 32 such that the force exerted by the probe element 32 will deflect the flexure 36 thereby giving rise to the generation of an electrical signal through changes in the characteristics of the strain gages 37 and 38.

With specific reference to FIG. 3, it will be noted that there are provided two strain gages 37 on the top of the flexure member 36 and similarly there are provided two strain gauges on the bottom only one of which is visible in FIG. 2. The two top strain gages 37 will be placed in tension when a force is applied, tending to flex the flexure 36 downwardly as viewed in FIG. 2 while the strain gages 38 will be placed in compression. These strain gages may be connected in a bridge arrangement in well known manner to thereby provide an output signal which is a function of the degree of flexing of the flexure and thus a function of the force applied by the probe 32.

Still referring to FIG. 2, it will now be evident that the force applied by the probe 32 on the flexure 36 is a function of the distance D between the spaced points on the specimen member to which the extensometer is secured. As an elongation occurs, the first member 12 will tend to separate from the second member 15 thereby moving the first cylinder 30 upwardly relative to the second cylinder 31. This action effectively decreases the action of the biasing spring 33 thereby lightening the force applied by the probe 32 on the flexure 36 resulting in the flexure 36 being flexed less than under the initial conditions. The electrical signal generated as a consequence of the strain gage bridge incorporating strain gages 37 and 38 will thus vary with changes in the distance D and the signal may be read out as a voltage which can be converted into direct units of elongation.

It will be clear from the description in FIG. 2 that the maximum range of readings occurs when the flexure element 36 is initially deflected to its maximum amount and then permitted to unflex to its relaxed horizontal position.

Referring to FIGS. 2, 4 and 5 it will be noted that the coupling element 35 includes internal threads cradling the helical turns of spring 33. The spring 33 can be initially rotated, causing an increase or decrease in the number of coils. This controls the proper deflection of spring 33, which together with the deflection of the strain gage flexure 36, has to equal the total elongation in addition to the original distance D. Also the biasing spring 33 will then exert the correct force onto the strain gage flexure 36, causing it to deflect the proper amount.

Another feature of the spring 33 is that it will act as a shock absorber to protect the strain gage flexure 36 in the event that the specimen 11 should rupture prior to attaining the predetermined maximum strain.

Finally, to provide a means of interchangeability between extensometers of different gage length or different maximum strain, into one recording device, a potentiometer is provided to control the exact millivolt per volt output of the strain gage bridge, for a given percent of maximum strain. This potentiometer is shown in FIG. 3 at 39 and is mounted in the second member 15. An opening 40 provides accessibility from the outside to make the proper adjustment of potentiometer 39.

OPERATION

The operation of the extensometer will be evident from the foregoing description. Initially, the device may be held with one hand, for example the operator's right hand and his thumb may engage the sleeve portion 27 of the manual arms 22 and 23 to retract the pins 20 and 21 all as described heretofore in FIG. 1. The V-shaped receiving knife edge portions of the members 12 and 15 can readily be moved to engage the specimen 11 at the spaced points and the arms 22 and 23 released, this action all being accomplished with one hand of the user to secure the extensometer to the member. The knife edges 13 and 26 will "bite" into the specimen at precise points which are exactly spaced at the given distance D.

As a load placing the specimen under tension is now applied to elongate the same, the first member 12 will gradually move apart from the second member 15, the movement being guided by the telescoping cylinders 30 and 31 as described in FIG. 2. As the member 12 moves upwardly relative to the member 15, the loading applied to the probe 32 by the spring 33 will gradually decrease so that the flexure member 36 will tend towards its normal unflexed horizontal position thereby relieving the strain on the strain gages 37 and 38 in a gradual manner. The decrease of load on the strain gage flexure results in a change of output signal from the strain gage bridge and, as stated, this signal may be converted to read directly the elongation of the specimen.

Should a rupture of the specimen occur, the shock of sudden separation is absorbed by the biasing spring 33 for the probe 32 and thus this spring serves a dual function in that it will act as a shock absorber as well as a means for adjusting the initial force applied by the probe to the flexure measuring portion of the system.

It will thus be seen, that the present invention has provided a vastly improved extensometer which can be manufactured relatively inexpensively and which is easily secured to specimens the extension of which is to be measured.

Minor changes falling within the scope and spirit of this invention will occur to those skilled in the art. The improved extensometer is therefore not to be thought of as limited to the specific embodiments set forth merely for illustrative purposes.

What is claimed is:

1. An extensometer for indicating the change in length of a specimen between first and second points, spaced a given distance apart along said specimen when said specimen is subject to a load, including, in combination:
   a. a first member defining a first gripping means for engaging said specimen at said first point;
   b. a second member defining a second gripping means for engaging said specimen at said second point;
   c. guide means coupling the first and second members together for movement towards and away from each other in response to changes in said given distance;
   d. a probe element;
   e. biasing means carried by said first member connected to said probe element for biasing said probe element towards and away from said second member; and
   f. strain gage flexure means carried by said second member in a position to be engaged by said probe element and responsive to the force exerted by said probe element to provide an electrical signal constituting a function of said force whereby changes in the distance between said first and second points on said specimen changes said force so that said electrical signal indicates the changes in said given distance.

2. An extensometer according to claim 1, in which said guide means includes first and second axially aligned cylinders carried by said first and second members respectively, said first cylinder being telescopically received in said second cylinder, said probe element being axially positioned in said first cylinder to extend through said second cylinder, said biasing means comprising a spring connected to said probe and coupled to the end of said first cylinder received in said second cylinder to thereby provide said biasing of said probe towards said second member.

3. An extensometer according to claim 2, in which said end of said first cylinder received in said second cylinder includes means for securing various portions of said spring to said end so that the effective length of said spring can be varied to thereby control the biasing force exerted by said probe element so that said force on the flexure means can be made initially the same.

4. An extensometer according to claim 2, in which said spring functions as a shock absorber should said specimen break suddenly when under a tension load.

5. An extensometer according to claim 1, in which the first and second gripping means include V-shaped receiving portions within which said spaced points on the specimen are seated; and, support means carrying opposed pins for engaging the opposite sides of the specimen to secure the specimen in the V-shaped receiving portions, said V-shaped receiving portions being defined by knife edges which precisely engage the specimen at said first and second points respectively whereby said given distance is precisely defined.

6. An extensometer according to claim 5, including means coupled to the support means for the pins and normally operable by one hand to simultaneously retract the pins from the V-shaped receiving portions to release the specimen.

7. An extensometer according to claim 6, including spring means on said support means for the pins normally biasing said pins towards said V-shaped receiving portions.

* * * * *